United States Patent [19]

Lekhtman

[11] Patent Number: 5,337,753
[45] Date of Patent: Aug. 16, 1994

[54] HEART RATE MONITOR

[75] Inventor: Gregory Lekhtman, Montreal, Canada

[73] Assignee: Biosig Instruments Inc., Montreal, Canada

[21] Appl. No.: 895,936

[22] Filed: Jun. 9, 1992

[51] Int. Cl.⁵ .............................................. A61B 5/04
[52] U.S. Cl. ..................... 128/706; 128/707
[58] Field of Search ............... 128/901, 902, 696, 706, 128/733, 707

[56] References Cited

U.S. PATENT DOCUMENTS

| | | | |
|---|---|---|---|
| 4,319,581 | 3/1982 | Cutter | 128/707 |
| 4,513,753 | 4/1985 | Tabata et al. | 128/706 |
| 4,825,874 | 5/1989 | Uhlemann | 128/696 |
| 4,913,146 | 4/1990 | DeCote, Jr. | 128/696 |

*Primary Examiner*—William E. Kamm
*Assistant Examiner*—Scott M. Getzow
*Attorney, Agent, or Firm*—Chilton, Alix & Van Kirk

[57] ABSTRACT

An elongate hollow cylindrical member houses electronic circuitry and has disposed on its surface, on either end, a live electrode and a spaced common electrode. The electronic circuitry includes a difference amplifier, and electromyogram signals detected by the electrodes are applied to opposite polarity inputs of the difference amplifier. As the electromyogram signals are of substantially equal amplitude and phase, the electromyogram signals will be subtracted from each other in the difference amplifier to provide a substantially zero output due to electromyogram signals at the output of the difference amplifier. However, electrocardiograph signals, being of opposite phase, will be added in the difference amplifier so that the output of the difference amplifier is substantially due to only the electrocardiograph signal.

16 Claims, 10 Drawing Sheets

HEART RATE MONITOR

BACKGROUND OF INVENTION

1. Field of the Invention

The invention relates to heart rate monitors for use in association with exercising apparatus and/or exercising procedures. More specifically, the invention relates to such a monitor which eliminates the effects of muscle artifact in the detection of a user's heart rate.

2. Description of Prior Art

Heart rate monitors for use in association with exercising apparatus and/or exercising procedures are known in the art, and one such monitor is illustrated in my U.S. Pat. No. Des. 254,569, Mar. 25, 1980, Lekhtman et al. My previous monitor, which is cylindrical in shape and which is grasped by both hands of a user, is designed to eliminate noise signals in the detection of a user's heart rate. However, such a monitor does not eliminate the effects of muscle artifact which is brought about when a user, in exercising, moves his arm or squeezes the monitor with his fingers. As electromyogram signals are in the same frequency range as electrocardiograph signals, the presence of these signals will affect the accuracy of the measured heart rate.

SUMMARY OF INVENTION

It is therefore an object of the invention to provide improved heart rate monitors for use in association with exercising apparatus and/or exercising procedures.

It is an even more specific object of the invention to provide such monitors which eliminate the effects of muscle artifact in the detection of a user's heart rate.

In accordance with the invention, the heart rate of a user is measured by measuring pulses in the hands of the user. The electromyogram signals of the hands of the users are applied to opposite polarity terminals of a difference amplifier, whereby the substantially equal amplitude and phase electromyogram signals are subtracted from each other to produce a zero level signal at the output of the differential amplifier.

In accordance with a particular embodiment of the invention there is provided a hear rate monitor for use by a user in association with exercise apparatus and/or exercise procedures, comprising:

an elongate member;

electronic circuitry including a difference amplifier having a first input terminal of a first polarity and a second input terminal of a second polarity opposite to said first polarity;

said elongate member comprising a first half and a second half;

a first live electrode and a first common electrode mounted on said first half in spaced relationship with each other;

a second live electrode and a second common electrode mounted on said second half in spaced relationship with each other;

said first and second common electrodes being connected to each other and to a point of common potential;

said first live electrode being connected to said first terminal of said difference amplifier and second live electrode being connected to said second terminal of said difference amplifier;

a display device disposed on said elongate member;

wherein, said elongate member is held by said user with one hand of the user on said first half contacting said first live electrode and said first common electrode, and with the other hand of the user on said second half contacting said second live electrode and said second common electrode;

whereby, a first electromyogram signal will be detected between said first live electrode and said first common electrode, and a second electromyogram signal, of substantially equal magnitude and phase to said first electromyogram signal will be detected between said first live electrode and said second common electrode;

so that, when said first electromyogram signal is applied to said first terminal and said second electromyogram signal is applied to said second terminal, the first and second electromyogram signals will be subtracted from each other to produce a substantially zero electromyogram signal at the output of said difference amplifier.

BRIEF DESCRIPTION OF DRAWINGS

The invention will be better understood by an examination of the following description, together with the accompanying drawings, in which:

FIGS. 4-1 to 4-7 comprise a flow chart of the program which drives the microprocessor of the inventive heart rate monitor;

DESCRIPTION OF PREFERRED EMBODIMENTS

Figure 1:
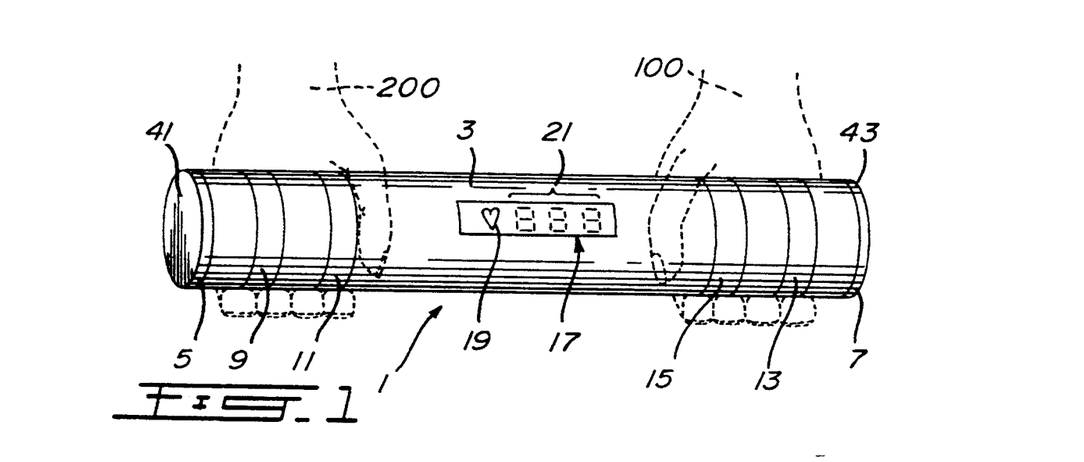
FIG. 1 is a perspective view of a heart rate monitor in accordance with the invention.

Turning now to FIG. 1, the heart rate monitor, illustrated generally at 1, comprises an elongate member, preferably, a cylindrical member 3 having a first half 5 and a second half 7. Disposed on the first half is a first live electrode 9 which comprises a ring member of a conductive material force-fit onto the cylindrical member. A first common electrode 11, which also comprises a ring member of a conductive material and which is also force-fit onto the cylindrical member, is also disposed on the first half and spaced from the first live electrode 9.

Disposed on the second half is a second live electrode 13, which, once again, comprises a ring member of a conductive material force-fit onto the cylindrical member, and a second common electrode, also comprising a ring member of a conductive material force-fit onto the cylindrical member and, once again, spaced from the second live electrode 13.

Preferably disposed in the middle of the cylindrical material is a display device 17 having a pulse indicator, preferably a heart 19, and a numerical indicator, illustrated at 21.

Plugs 41 and 43, inserted at either end of the cylindrical member are preferably elasticized and force-fit into the member so that the cylindrical member is waterproofingly sealed.

Figure 2:
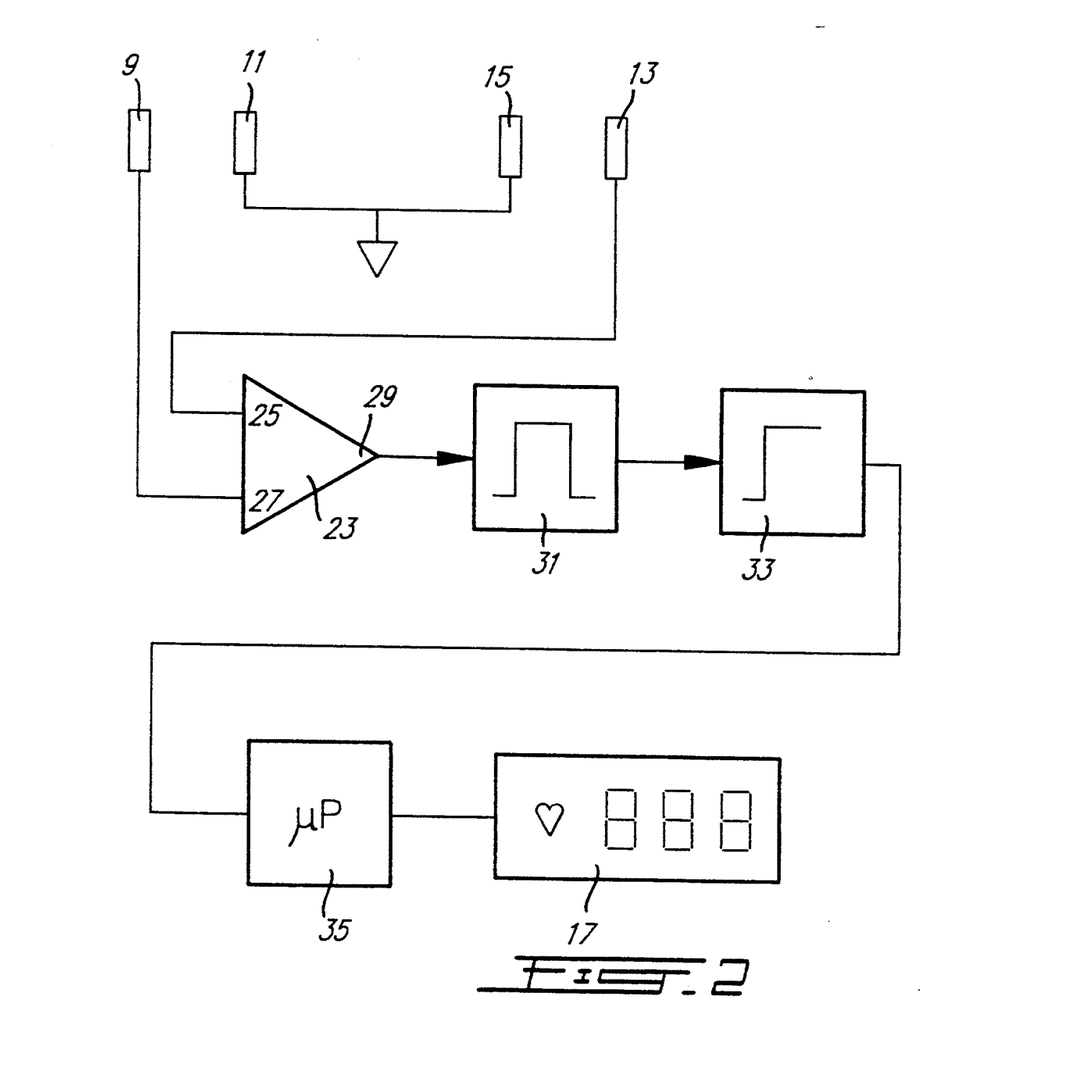
FIG. 2 illustrates in block diagram form the electronic circuitry for carrying out the measurements in the inventive heart rate monitor.

Turning now to FIG. 2, as can be seen, common electrodes 11 and 15 are connected to each other and to a point of common potential, for example, ground. Live electrode 9 is connected to one input 27 of a difference amplifier 23, and live electrode 13 is connected to a second input, 25, of the difference amplifier 23. The inputs 25 and 27 can comprise a positive and a negative input respectively or vice-versa. In any case, inputs 25 and 27 are of opposite polarity.

Output 29 of the difference amplifier is connected to a bandpass filter 31. The bandpass filter will extract "R" waves from the electrocardiograph signals.

The output of filter 31 is connected to a threshold limiter 33 which produces a 200 msec square pulse synchronized with each R wave. The level of limiter 33 is automatically adjusted to the average amplitude of the R wave. The output of 33 is fed to a microprocessor 35 which is driven by the program illustrated in FIGS. 4-1 to 4-7 herein. The display 17 is driven by the microprocessor 35 as will be seen in the description of FIGS. 4-1 to 4-7.

In operation, the left-hand 100 of the user is placed over both electrodes 13 and 15 so that it is in physical and electrical contact with both electrodes. In the same way, the right-hand 200 of the user is placed over the electrodes 9 and 11 so that it is in physical and electrical contact with both electrodes.

Noise received by the electrodes 9 and 11 will be of substantially equal amplitude and substantially equal phase to the noise received by the electrodes 13 and 15. Thus, the noise signals will be subtracted from each other in the difference amplifier 23 to thereby be cancelled in the difference amplifier.

The electromyogram signals received by electrodes 9 and 11 will also be of substantially equal magnitude and phase to the electromyogram signals received by the electrodes 13 and 15. Accordingly, they will also be cancelled out in the difference aplifier 23.

However, the electrocardiograph signals received by the electrodes 9 and 11 are of opposite phase to the electrocardiograph signals received by the electrodes 13 and 15. Accordingly, the electrocardiograph signals will be added to each other in the difference amplifier 23, so that the output of 23 is substantially dependent only on the electrocardiograph signals.

In accordance with one embodiment of the invention, cylindrical member 3 is hollow, and the electronic circuitry is mounted in the hollow interior of the member 3.

Figure 3:
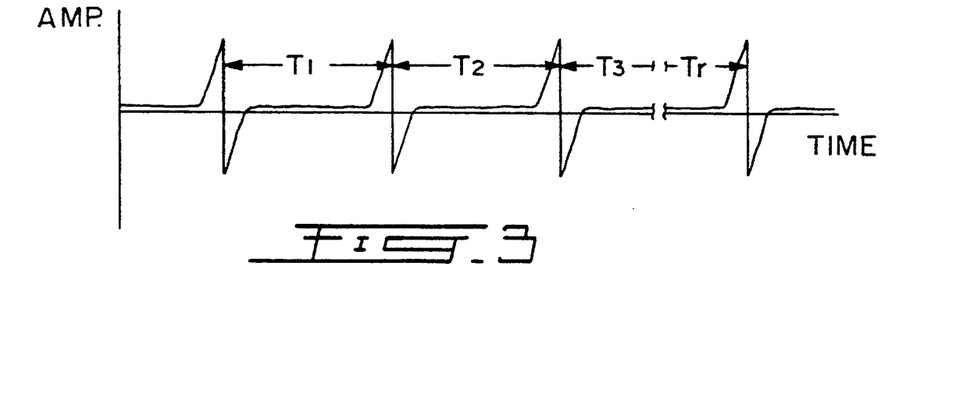
FIG. 3 is a graph of an electrocardiograph useful in understanding the operation of the present heart rate monitor.

FIG. 3 illustrates such electrocardiograph signals. As can be seen, the heart pulses are separated from each other in time by times T1, T2, T3 ... Tn. The magnitudes of T1, T2, T3 ... Tn are typically of approximately the same value under any given condition.

In accordance with the invention, the pulse indicator 19 is illuminated on receipt of each pulse in the electrocardiograph signal. A pulse rate numerical display is calculated by using four adjacent time measurements. Each measurement is verified for correctness by comparing it with a previous measurement. If a current measurement is less than 85% of the previous measurement or greater than 115% of a previous measurement, then it is considered an inaccuracy either in the measurement or in breakthrough of noise signals and is discarded in calculating the average.

As seen in FIGS. 4-1 to 4-7, in the microprocessor, each time a pulse is detected, the pulse indicator on the display is illuminated. Every time a pulse is detected, a time count is begun and the computer then monitors for the next pulse. When the next pulse is detected, the time counted in the computer between the two pulses is stored and a new time count begins. When a third pulse is detected, the second time measurement is stored, and in a similar manner, the third and fourth time measurements are stored.

The time measurements are then compared each to its previous one. If a time measurement is greater than 115% of the previous measurement or less than 85% of the previous measurement, that measurement is deleted. The remaining measurements in four adjacent measurements are then averaged, and this average value then drives the display to illuminate the numerics.

If the second, third and fourth measurements are all either greater than 115% of the first or all less than 85% of the first measurement, then the first measurement must be suspect and an average is not calculated for that particular cycle. In fact, an average is calculated only if there are at least two valid measurements in the cycle.

The cycle keeps repeating itself to provide new values for continuously driving and refreshing the numerical display.

Figure 5:
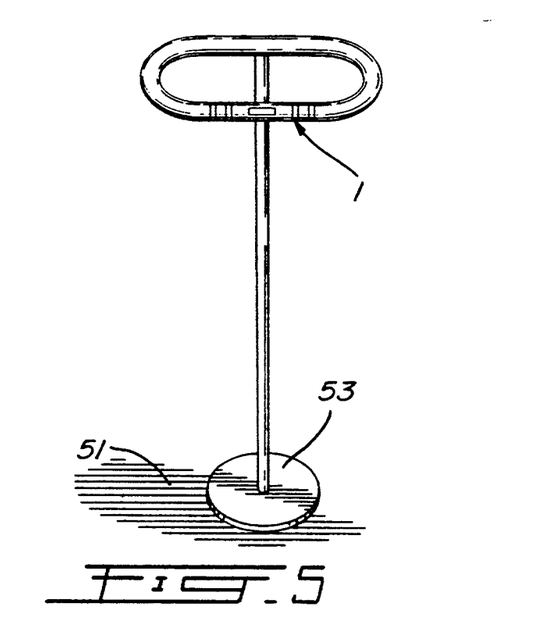
FIG. 5 illustrates a floor mounted heart rate monitor.
Figure 6:
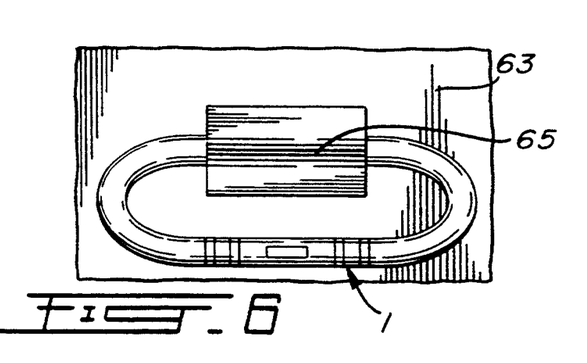
FIG. 6 illustrates a wall mounted heart rate monitor.

The heart rate monitor in accordance with the invention can be held by a user when performing exercising procedures such as jogging or the like. Alternatively, it could be adapted to be mounted on a floor 51 as illustrated in FIG. 5. In the FIG. 5 embodiment, the monitor is mounted on a base 53 which is then disposed on the floor.

Figure 7:
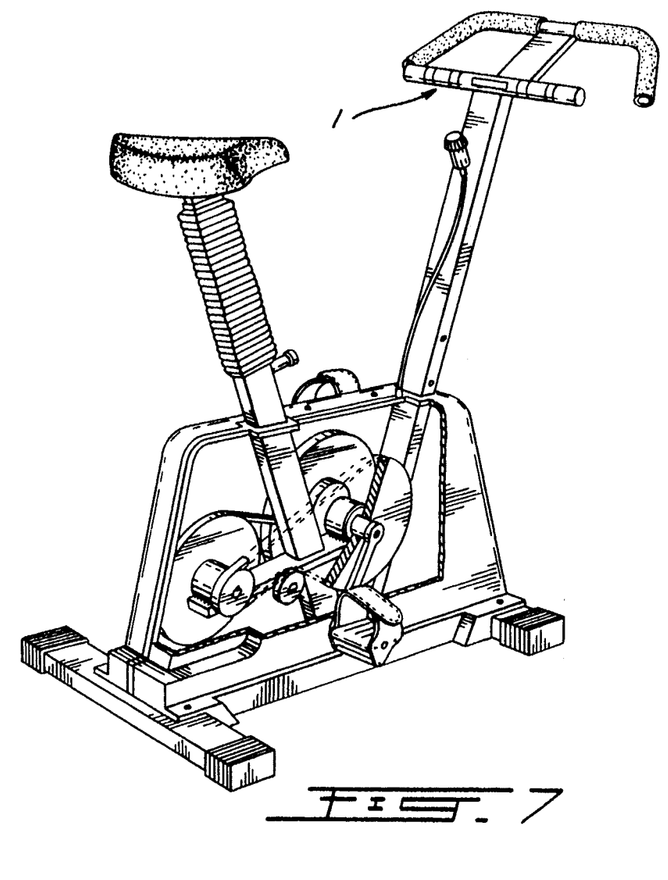
FIG. 7 illustrates a heart rate monitor mounted on an exercising bicycle.

It is also possible to provide a monitor for mounting on a wall 63 as illustrated in FIG. 7. Once again, the monitor would be mounted on a base 65 which would then be mounted on the wall 63.

Figure 8:
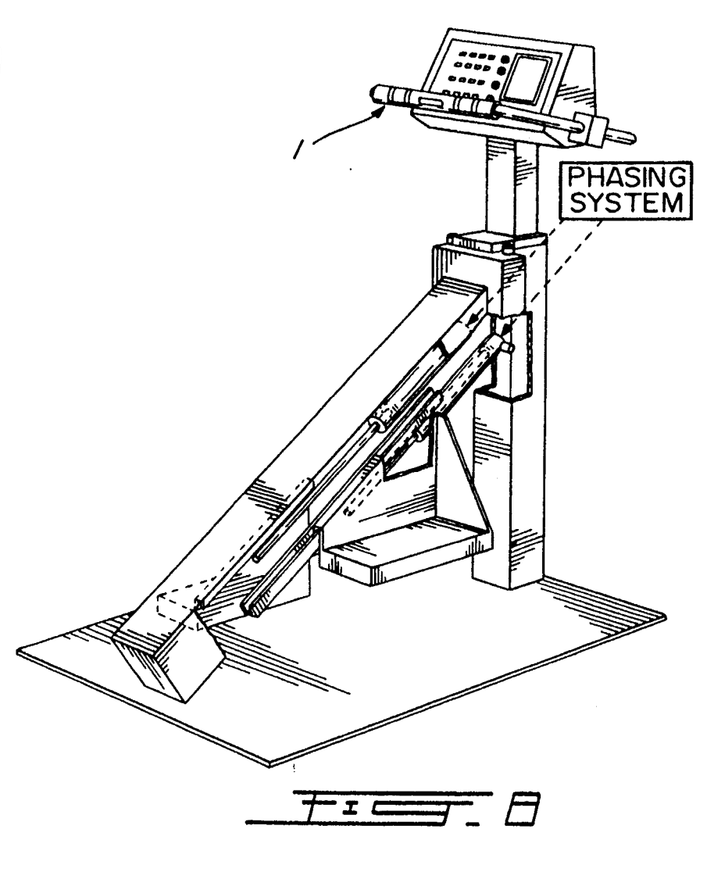
FIG. 8 illustrates a heart rate monitor used in association with a stair climbing exercise apparatus.

As illustrated in FIG. 7, the heart rate monitor could also be mounted on an exercycle, and it could be integrated with or it can comprise the handle bar of the exercycle. The heart rate monitor could also be incorporated in a stair climbing exercise apparatus as illustrated in FIG. 8. The heart rate monitor would comprise or be integrated with the handle which is held by the exerciser.

In the FIGS. 7 and 8 embodiments, although the electronic circuitry could be housed in the elongate member 3, it could also be housed in the apparatus itself, for example, with other electronic circuitry used by the apparatus. In that case, there would still exist the connections between the electrodes and the difference amplifier, and the microprocessor and the display, which would still be on the elongate member.

Accordingly, it can be seen that the heart rate monitor in accordance with the invention can either be carried by an exerciser as a stand-alone unit, or it could be adapted to be mounted on a floor or on a wall. It also could be adapted to comprise a part of an exercise apparatus. In addition, the particular floor or wall mountings and exercise apparatus illustrated are only examples, and the monitor can be used with other mountings and exercise apparatus.

Figure 9:
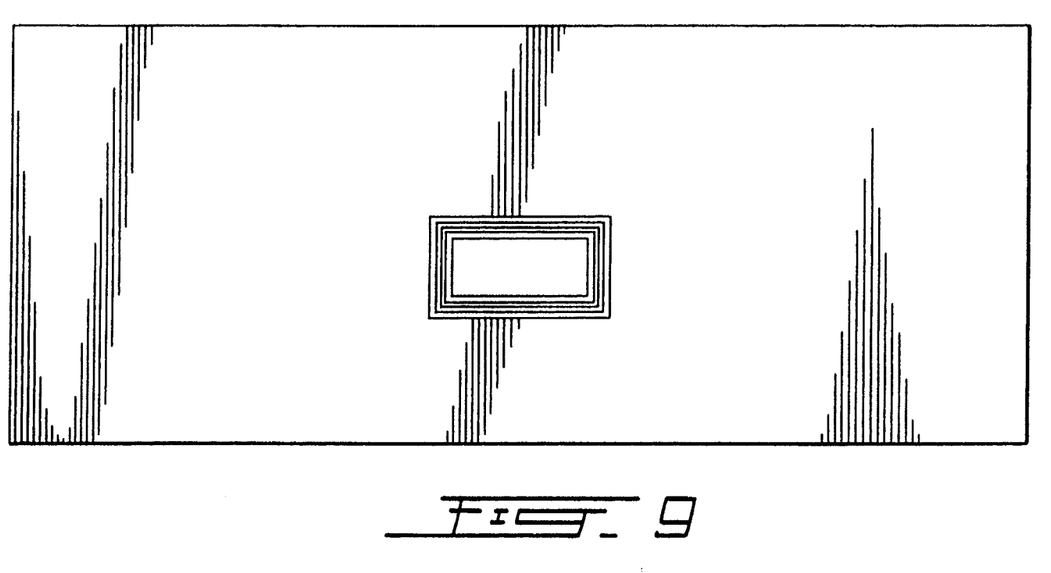
FIG. 9 illustrates an insert which can be inserted into the tubular member.
Figure 41:
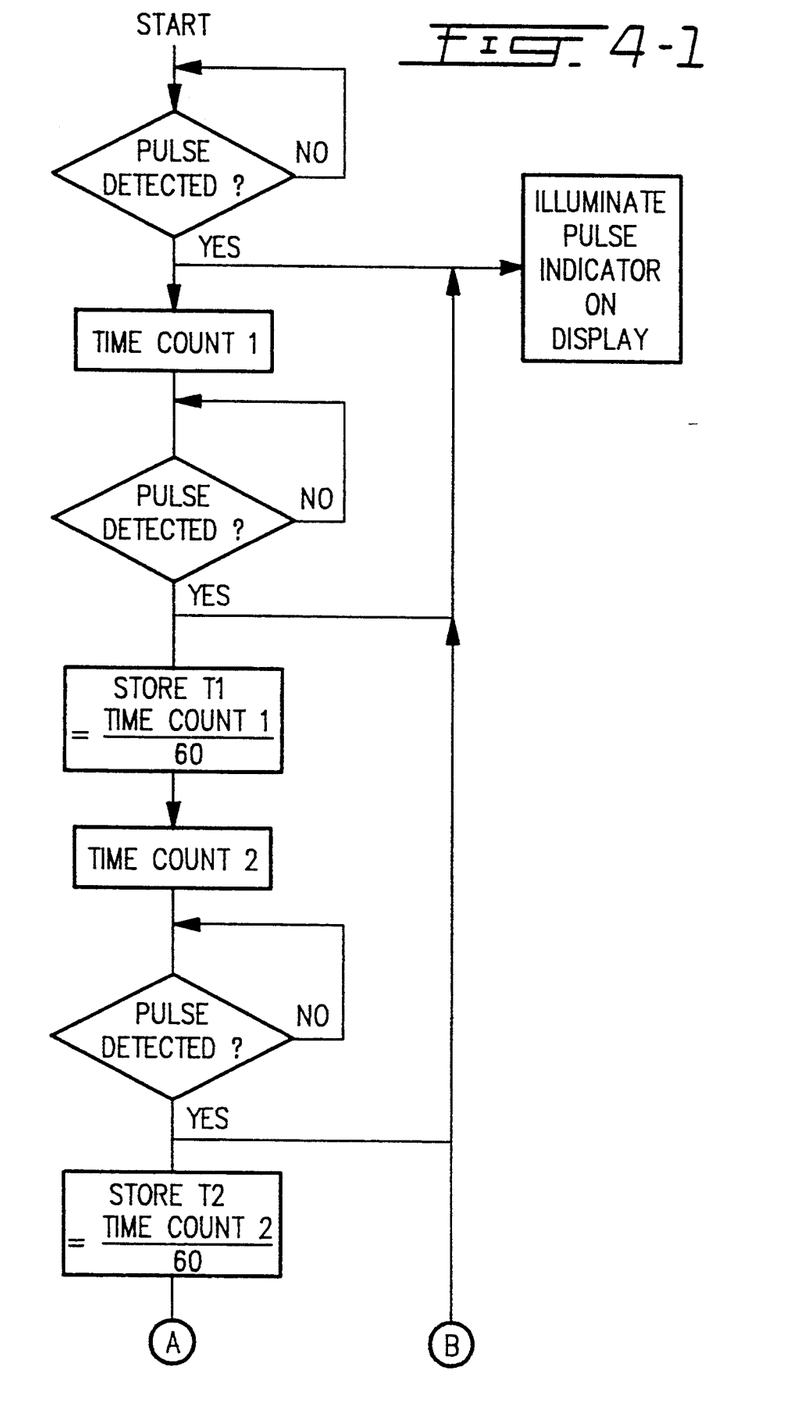
Figure 42:
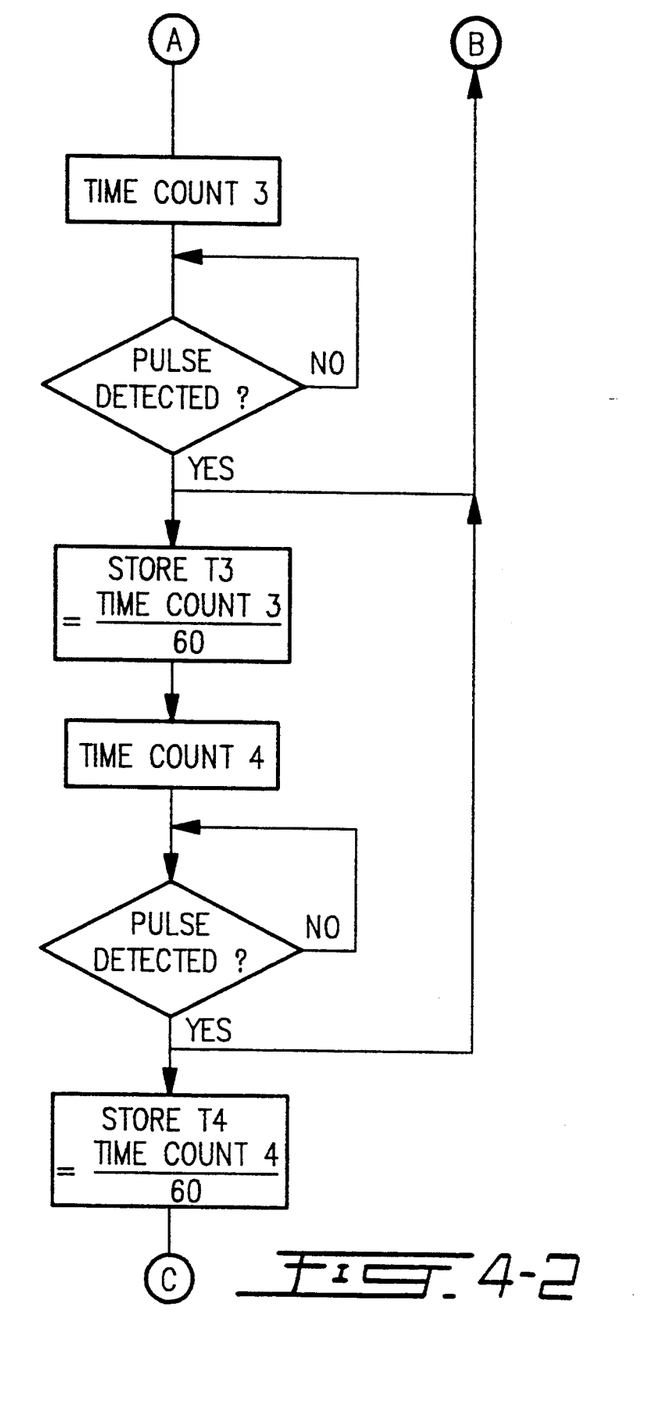
Figure 43:
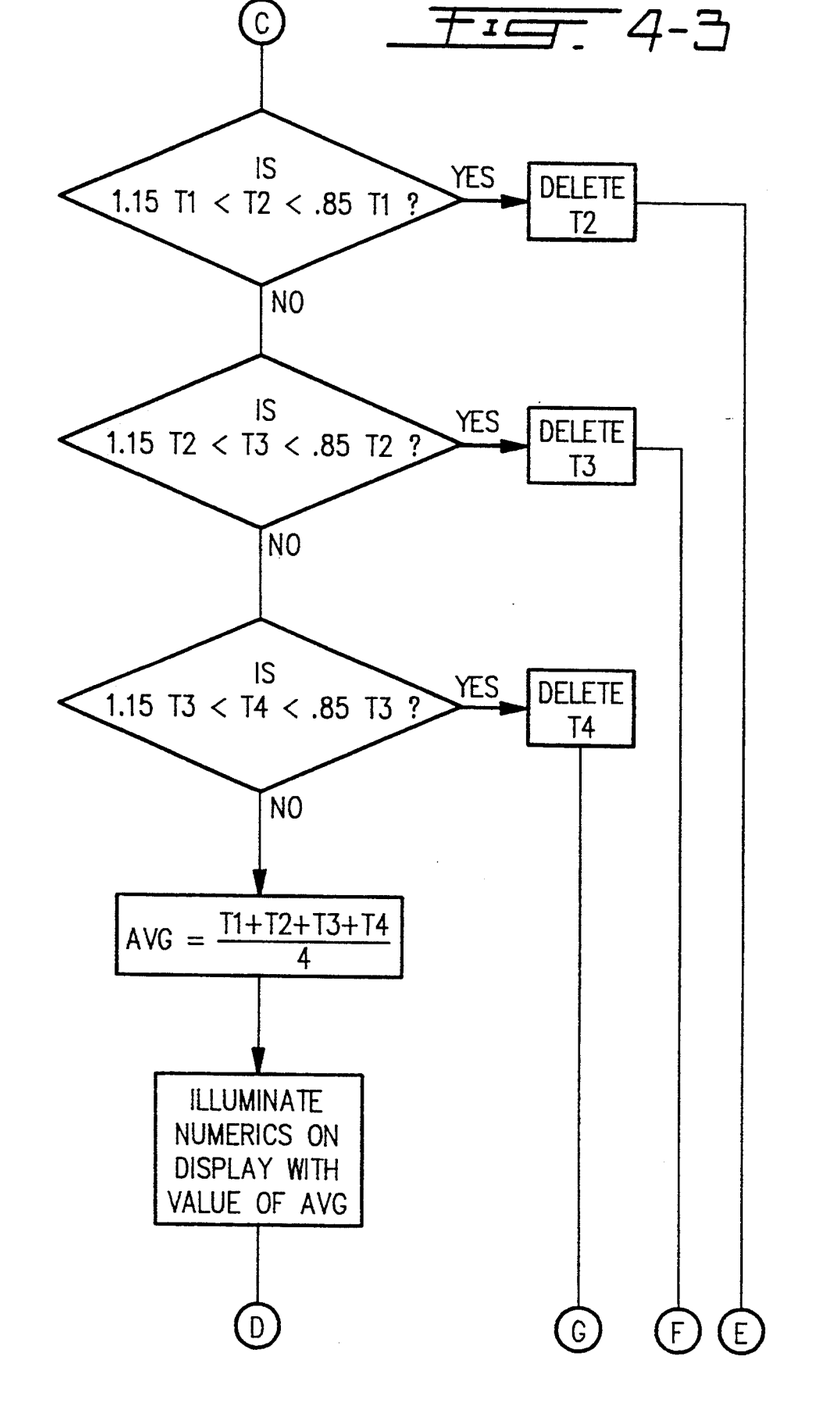
Figure 44:
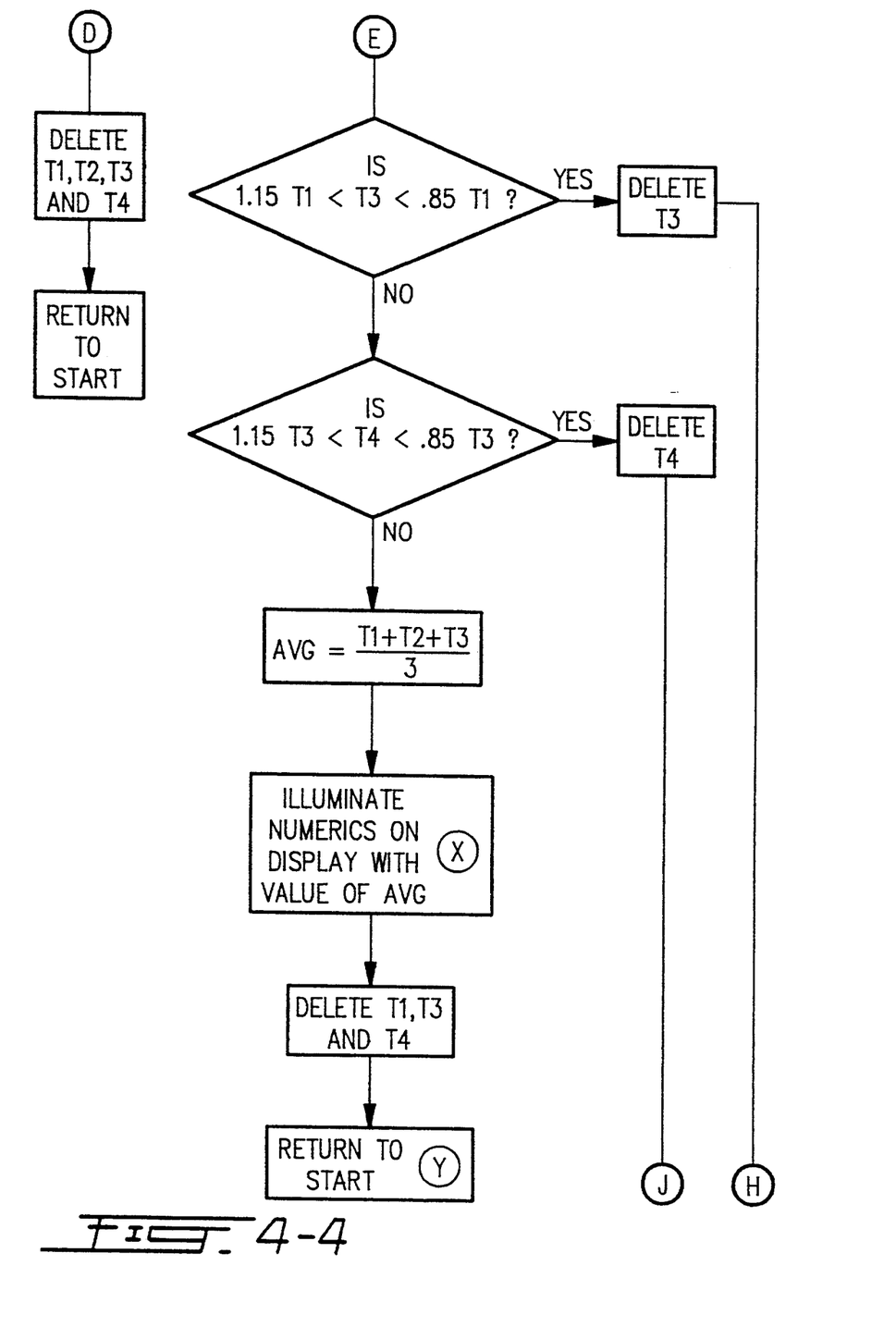
Figure 45:
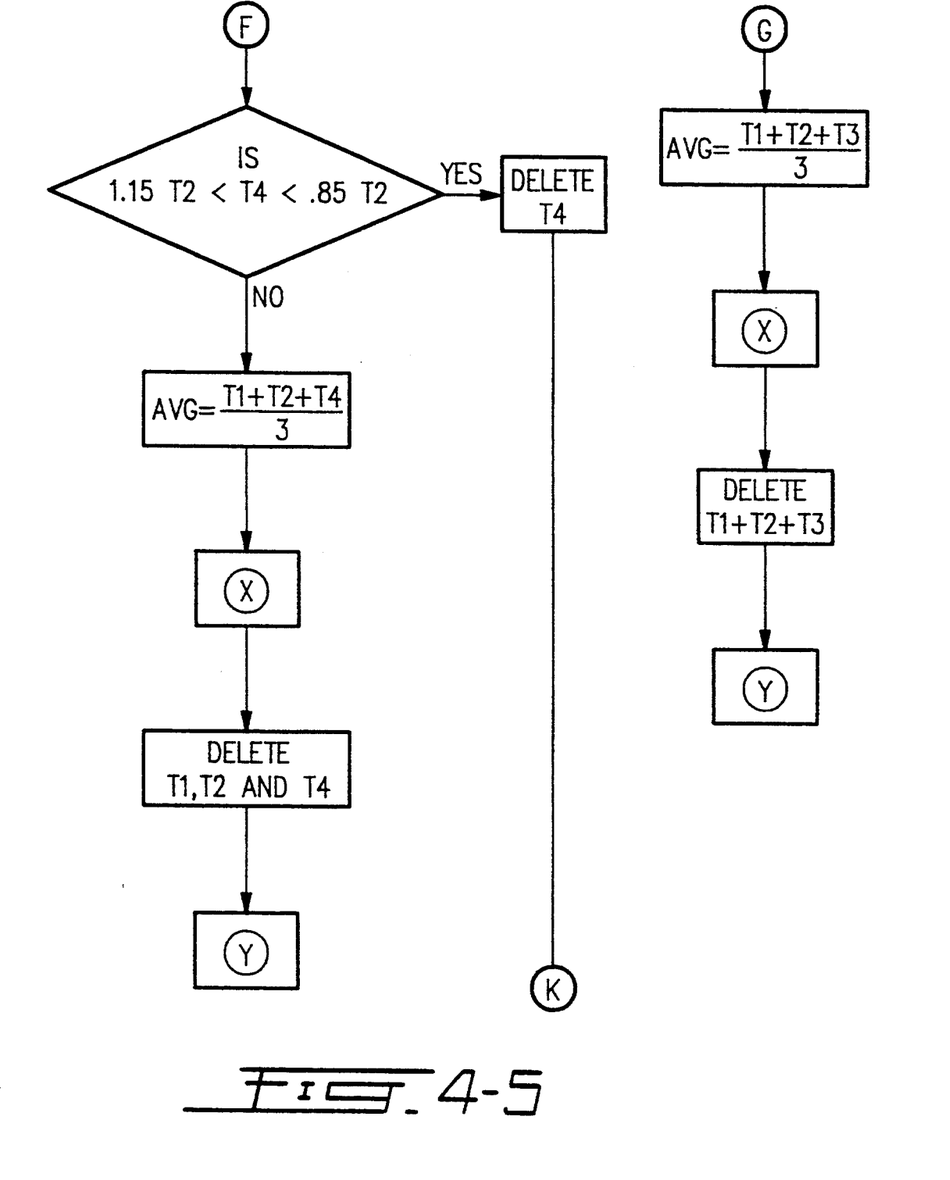
Figure 46:
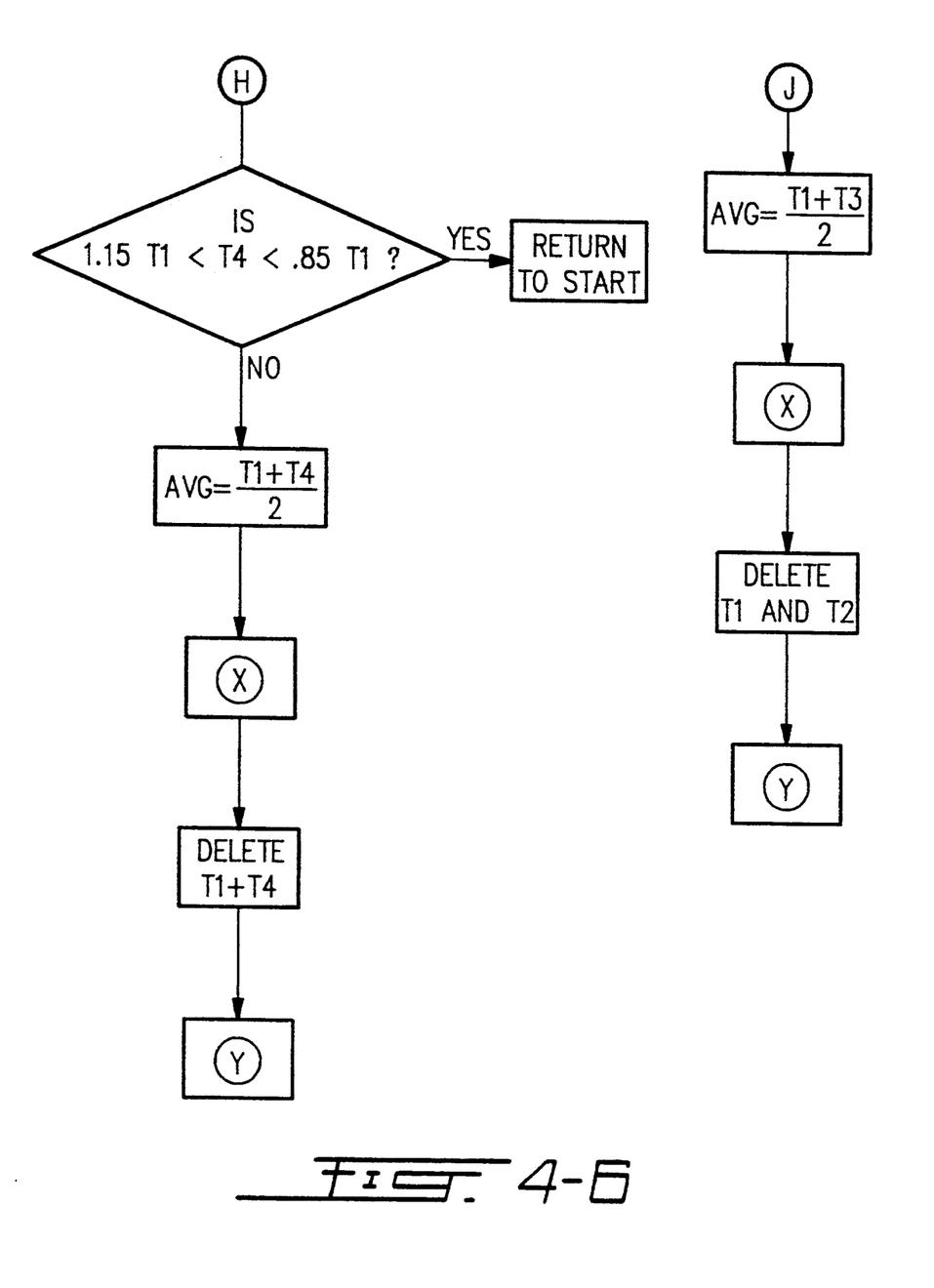
Figure 47:
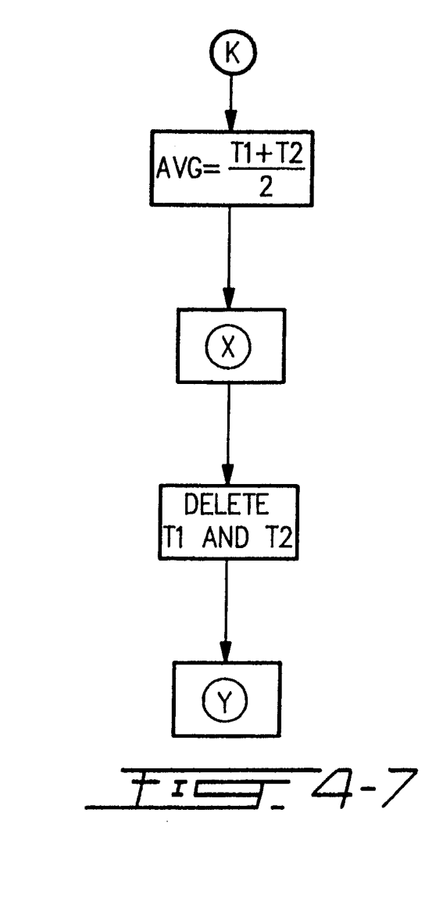

Also, in accordance with the invention, a paper insert, such as illustrated in FIG. 9, can be inserted within the tubular member 3. The insert can contain the product's name, for example, INSTA PULSE TM, as well as other graphics and legends. The paper insert would be rolled up with the graphics on the top surface and slid into the tubular member which would comprise a transparent material so that all of the information imprinted on the insert would be seen through the top surface of the tubular member.

Further, although the electrodes have been illustrated as rings, other configurations, e.g. half rings, spaced plates, etc. could be used.

Although several embodiments have been described, this was for the purpose of illustrating, but not limiting, the invention. Various modifications, which will come readily to the mind of one skilled in the art, are within the scope of the invention as defined in the appended claims.

I claim:

1. A heart rate monitor for use by a user in association with exercise apparatus and/or exercise procedures, comprising;
    an elongate member;
    electronic circuitry including a difference amplifier having a first input terminal of a first polarity and a second input terminal of a second polarity opposite to said first polarity;
    said elongate member comprising a first half and a second half;
    a first live electrode and a first common electrode mounted on said first half in spaced relationship with each other;
    a second live electrode and a second common electrode mounted on said second half in spaced relationship with each other;
    said first and second common electrodes being connected to each other and to a point of common potential;
    said first live electrode being connected to said first terminal of said difference amplifier and said second live electrode being connected to said second terminal of said difference amplifier;
    a display device disposed on said elongate member;
    wherein, said elongate member is held by said user with one hand of the user on said first half contacting said first live electrode and said first common electrode, and with the other hand of the user on said second half contacting said second live electrode and said second common electrode;
    whereby, a first electromyogram signal will be detected between said first live electrode and said first common electrode, and a second electromyogram signal, of substantially equal magnitude and phase to said first electromyogram signal will be detected between said second live electrode and said second common electrode;
    so that, when said first electromyogram signal is applied to said first terminal and said second electromyogram signal is applied to said second terminal, the first and second electromyogram signals will be subtracted from each other to produce a substantially zero electromyogram signal at the output of said difference amplifier;
    and whereby a first electrocardiograph signal will be detected between said first live electrode and said first common electrode and a second electrocardiograph signal, of substantially equal magnitude but of opposite phase to said first electrocardiograph signal will be detected between said second live electrode and said second common electrode;
    so that, when said first electrocardiograph signal is applied to said first terminal and said second electrocardiograph signal is applied to said second terminal, the first and second electrocardiograph signals will be added to each other to produce a non-zero electrocardiograph signal at the output of said difference amplifier;
    means for measuring time intervals between heart pulses on detected electrocardiograph signal;
    means for calculating the heart rate of said user using said measure time intervals;
    said means for calculating being connected to said display device;
    whereby, the heart rate of said user is displayed on said display device.

2. A monitor as defined in claim 1 wherein said elongate member comprises a hollow cylindrical member;
    said electronic circuitry being housed in the interior of said hollow cylindrical member.

3. A monitor as defined in claim 2 wherein said first live electrode comprises a first ring member of a conductive material mounted on said first half of said elongate member, and wherein said first common electrode comprises a second ring member of a conductive material mounted on said first half of said elongate member and spaced from said first ring member;
    and wherein said second live electrode comprises a third ring member of a conductive material mounted on said second half of said elongate member and wherein said second common electrode comprises a fourth ring member of a conductive material mounted on said second half of said elongate member and spaced from said third ring member.

4. A monitor as defined in claim 3 and wherein said means for measuring time intervals comprises;
    a bandpass filter, the output of said difference amplifier being connected to an input of said bandpass filter;
    a threshold limiter, the output of said bandpass filter being connected to an input of said threshold limiter;
    and wherein said means for calculating the heart rate comprises;
    a microprocessor, the output of said threshold limiter being connected to an input of said microprocessor;
    the output of said microprocessor being connected to said display device.

5. A monitor as defined in claim 4 wherein said display device comprises;
    a pulse indicator adapted to be illuminated each time a heart pulse of the user is detected; and
    a pulse rate indicator comprising a numerical indication of the pulse rate of the user.

6. A monitor as defined in claim 5 and comprising elasticized plugs force-fit into both ends of said cylindrical member;
    whereby, the interior of said hollow cylindrical member is waterproofingly sealed.

7. A monitor as defined in any one of claims 1 or 6 and including a stand means for mounting the monitor on the floor;
    said stand means including a base and an upwardly extending member.

8. A monitor as defined in any one of claims 1 or 6 and including a means for mounting said monitor on a wall;

said means comprising a base.

9. A monitor as defined in any one of claims 2 or 6 and including insert means;
   said insert means comprising a paper-like material having graphics and alphabetic information imprinted on one surface thereof;
   said hollow cylindrical member comprising a transparent material;
   said insert means being inserted into said hollow cylindrical member such that the graphics are disposed against the wall of said hollow cylindrical member so that said graphics can be seen on the outside of said hollow cylindrical member.

10. A monitor as defined in claim 6 wherein said cylindrical member is mounted on an exercise apparatus.

11. A monitor as defined in claim 1 wherein said elongate member is mounted on an exercise apparatus;
    said electronic circuitry being mounted in said exercise apparatus.

12. A monitor as defined in claim 11 wherein said elongate member comprises a hollow cylindrical member.

13. A monitor as defined in claim 12 wherein said first live electrode comprises a first ring member of a conductive material mounted on said first half of said elongate member, and wherein said first common electrode comprises a second ring member of a conductive material mounted on said first half of said elongate member and spaced from said first ring member;
    and wherein said second live electrode comprises a third ring member of a conductive material mounted on said second half of said elongate member and wherein said second common electrode comprises a fourth ring member of a conductive material mounted on said second half of said elongate member and spaced from said third ring member.

14. A monitor as defined in claim 13 and wherein said electronic circuitry further includes;
    a bandpass filter, the output of said difference amplifier being connected to an input of said bandpass filter;
    a threshold limiter, the output of said bandpass filter being connected to an input of said threshold limiter;
    a microprocessor, the output of said threshold limiter being connected to an input of said microprocessor;
    the output of said microprocessor being connected to said display device.

15. A monitor as defined in claim 14 wherein said display device comprises;
    a pulse indicator adapted to be illuminated each time a heart pulse of the user is detected; and
    a pulse rate indicator comprising a numerical indication of the pulse rate of the user.

16. A monitor as defined in claim 15 and comprising elasticized plugs force-fit into both ends of said cylindrical member;
    whereby, the interior of said hollow cylindrical member is waterproofingly sealed.

* * * * *

(12) EX PARTE REEXAMINATION CERTIFICATE (7853rd)
United States Patent
Lekhtman (10) Number: US 5,337,753 C1
(45) Certificate Issued: Nov. 9, 2010

(54) HEART RATE MONITOR

(75) Inventor: Gregory Lekhtman, Montreal (CA)

(73) Assignee: Biosig Instruments Inc., Montreal, Quebec (CA)

Reexamination Request:
No. 90/010,366, Dec. 19, 2008
No. 90/010,612, Jul. 17, 2009

Reexamination Certificate for:
Patent No.: 5,337,753
Issued: Aug. 16, 1994
Appl. No.: 07/895,936
Filed: Jun. 9, 1992

(51) Int. Cl.
*A61B 5/024* (2006.01)
*A61B 5/0408* (2006.01)
*A61B 5/0245* (2006.01)
*A61B 5/22* (2006.01)

(52) U.S. Cl. .................................. 600/519; 600/520
(58) Field of Classification Search .................. None
See application file for complete search history.

(56) References Cited

U.S. PATENT DOCUMENTS

| | | | |
|---|---|---|---|
| 4,051,522 A | 9/1977 | Healy et al. | |
| 4,233,965 A | 11/1980 | Fairbanks | |
| 4,248,244 A | 2/1981 | Charnitski et al. | |
| 4,444,200 A | 4/1984 | Fujisaki et al. | |
| 4,898,182 A | 2/1990 | Hawkins et al. | |

OTHER PUBLICATIONS

Goldman and Klatz, *The "E" Factor*; pp. 240–247; 1988.
Specimen of U.S. Trademark Registration No. 1,156,243; 4 pp.; registered Jun. 2, 1981.
Strong; *Biophysical Measurements*; pp. 264–295; Jun. 1971.
U.S. Trademark Registration No. 1,156,423 to Biosig Inc., Jun. 2, 1981.
De Vel, "R–Wave Detection in the Presence of Muscle Artifacts," *IEEE Transactions on Biomedical Engineering*, vol. BME–31, Nov. 1984, pp. 715–717.
Thakor, "Electrical Interference in Biopotential Recording," *Encyclopedia of Medical Instrumentation*, 1988, pp. 1014–1017.
Trademark Specimen, dated Nov. 14, 1978, filed by Biosig Instruments.

*Primary Examiner*—Alexander J Kosowski (57) ABSTRACT

An elongate hollow cylindrical member houses electronic circuitry and has disposed on its surface, on either end, a live electrode and a spaced common electrode. The electronic circuitry includes a difference amplifier, and electromyogram signals detected by the electrodes are applied to opposite polarity inputs of the difference amplifier. As the electromyogram signals are of substantially equal amplitude and phase, the electromyogram signals will be subtracted from each other in the difference amplifier to provide a substantially zero output due to electromyogram signals at the output of the difference amplifier. However, electrocardiograph signals, being of opposite phase, will be added in the difference amplifier so that the output of the difference amplifier is substantially due to only the electrocardiograph signal.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claim 1-16 is confirmed.

* * * * *